United States Patent [19]

Watanabe

[11] Patent Number: 4,781,673

[45] Date of Patent: Nov. 1, 1988

[54] BRAIN VENTRICLE SHUNT SYSTEM WITH FLOW-RATE SWITCHING MECHANISM

[75] Inventor: Yasuo Watanabe, Komae, Japan

[73] Assignee: Kabushiki Kaisha Nihon M.D.M., Tokyo, Japan

[21] Appl. No.: 938,926

[22] Filed: Dec. 8, 1986

[30] Foreign Application Priority Data

Dec. 20, 1985 [JP] Japan ................................ 60-286950
Oct. 22, 1986 [JP] Japan ................................ 61-25138

[51] Int. Cl.$^4$ .............................................. A61M 5/00
[52] U.S. Cl. ........................................ 604/9; 604/247
[58] Field of Search ........................ 604/8–10, 604/247; 137/504, 505, 505.11, 511, 512, 516.11, 527, 529; 222/17, 96, 97, 633, 209–212

[56] References Cited

U.S. PATENT DOCUMENTS

| | | | |
|---|---|---|---|
| 3,768,508 | 10/1973 | Schulte | 604/9 |
| 3,827,439 | 8/1974 | Schulte et al. | 604/9 |
| 3,985,140 | 10/1976 | Harris | 604/9 |
| 4,615,691 | 10/1986 | Hakim et al. | 604/9 |
| 4,627,832 | 12/1986 | Hooven et al. | 604/9 |
| 4,636,194 | 1/1987 | Schulte et al. | 604/9 |
| 4,681,559 | 7/1987 | Hooven | 604/9 |

Primary Examiner—Barry S. Richman
Assistant Examiner—T. J. Wallen
Attorney, Agent, or Firm—Schwartz & Weinrieb

[57] ABSTRACT

A brain ventricle shunt system provided with a flow-rate switching mechanism is used as a brain ventricle-peritoneum shunt or a brain ventricle-auricle shunt. It is surgically implanted in the body of a hydrocephalic patient or the like. It is constructed of a check valve for preventing the cerebro-spinal fluid from flowing back to the brain ventricle and a flow-rate switching mechanism for switching the flow rate of cerebro-spinal fluid to be fed from the brain ventricle catheter to the peritoneum or auricle catheter. The switching mechanism is provided with flow passages connected to one another in parallel, flow-rate regulators interposed respectively in the flow passages to control the flow rates through the respective flow passages to predetermined flow rates, and on-off valves interposed respectively in the flow passages so as to shut off the flow passages individually upon the application of external drive forces thereto. The system has merit in that the switching operation of the flow rate, which has been considered difficult, can be achieved very easily and safely. It permits switching of the flow rate among many levels without failure. The flow-rate controlling position can be precisely determined either visually or palpably through the scalp.

20 Claims, 6 Drawing Sheets

F I G. 3(a) 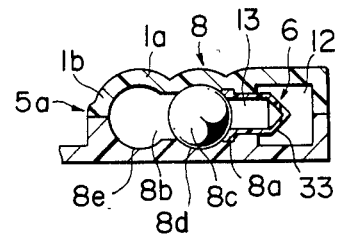
F I G. 3(b) 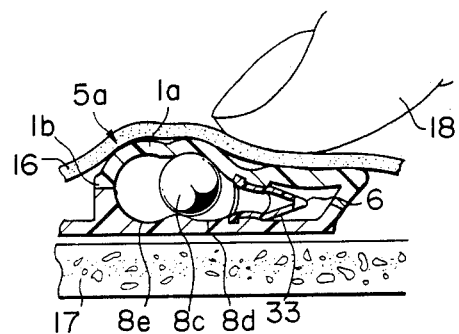
F I G. 3(c) 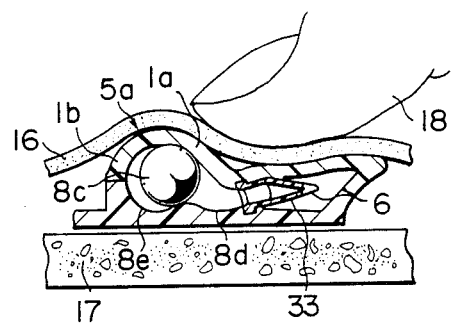
F I G. 3(d) 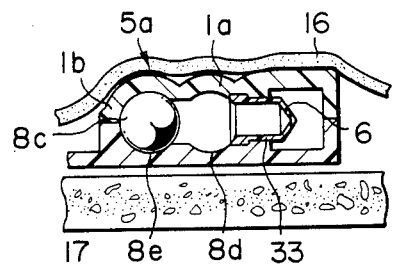

F I G.11(a)
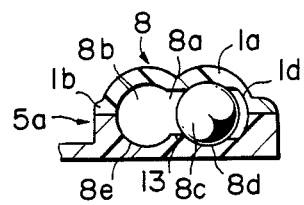
F I G.11(b)
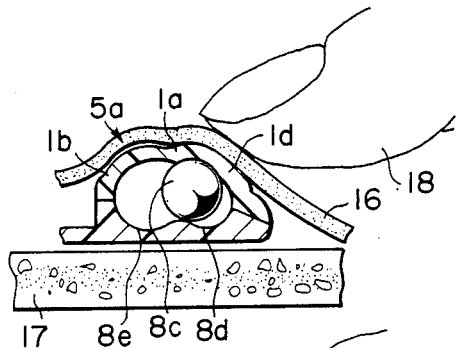
F I G.11(c)
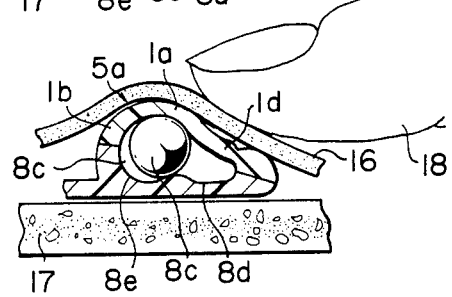
F I G.11(d)
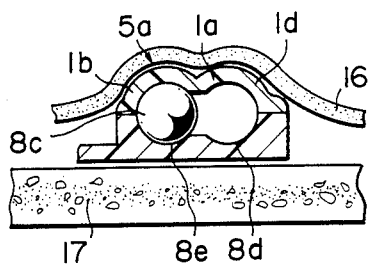

F I G. 12
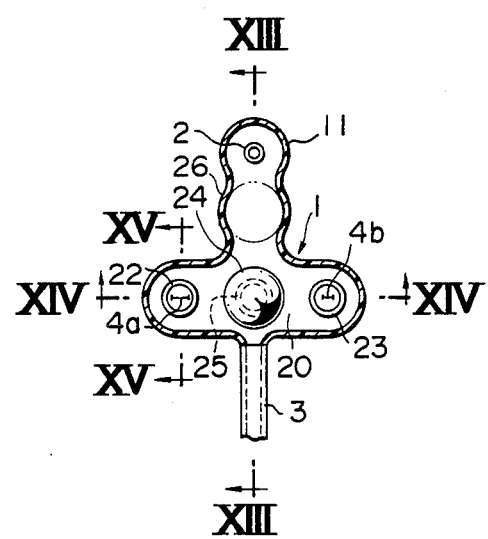
F I G. 13
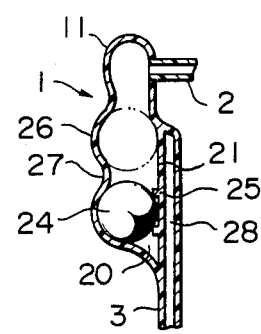
F I G. 14
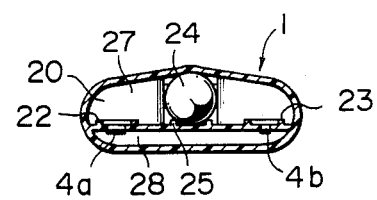
F I G. 15
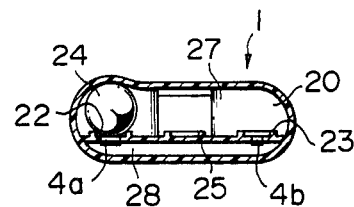
F I G. 16
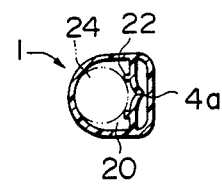

BRAIN VENTRICLE SHUNT SYSTEM WITH FLOW-RATE SWITCHING MECHANISM

BACKGROUND OF THE INVENTION (1) Field of the Invention

This invention relates generally to a brain ventricle-peritoneum shunt or brain ventricle-auricle shunt (hereinafter called "brain ventricle shunt") surgically implanted in the body of a hydrocephalic patient or the like, and more especially, to a brain ventricle shunt which permits or facilitates a switch in the flow rate of the cerebro-spinal fluid.

(2) Description of the Prior Art

A brain ventricle shunt is generally constructed of a fine tubular brain ventricle catheter which is adapted to be inserted into the brain ventricle, a shunt main body (relay chamber) connected to the brain ventricle catheter and including a reservoir and a pump chamber, and a tubular peritoneum or auricle catheter connected to the shunt main body and which is adapted to be inserted into the peritoneum or the auricle.

The shunt main body is implanted on the skull under the scalp. Inside the shunt main body, there is provided a relief valve composed of a miter valve or the like, which is closed and opened by means of the pressure of the cerebro-spinal fluid, which is an excrement fluid from the brain ventricle. This relief valve serves to regulate the flow rate of the cerebro-spinal fluid owing to its function as a flow-rate regulator and also serves to function as a check valve.

Examples of conventional brain ventricle shunts are disclosed within U.S. Pat. No. 3,827,439 issued to Schulte at al. and entitled "Plug Valve For Physiological Shunt Systems" and U.S. Pat. No. 3,769,982 issued to Shulte and entitled "Physiological Drainage System With Closure Means Responsive to Downstream Suction".

On occasion, a need may arise to adjust the flow rate of the cerebro-spinal fluid, which is regulated by the above-mentioned check valve, after implantation of a brain ventricle shunt. Since the flow rate of the cerebro-spinal fluid is regulated at a fixed level due to the use of a single relief valve in a conventional brain ventricle shunt, the conventional brain ventricle shunt is accompanied by the problem that the shunt main body, which has been implanted in the head or the like of a patient, must be surgically removed so that its relief valve can then be replaced by means of another relief valve having a regulated flow rate of a different level.

OBJECT OF THE INVENTION

With the foregoing in mind, this invention has as its principal object the provision of a brain ventricle shunt with a flow-rate switching mechanism which permits the switching of its flow rate of the cerebro-spinal fluid by means of an external drive forces in accordance with a simple procedure without the need for replacement of the shunt main body which is implanted in the body of a patient.

SUMMARY OF THE INVENTION

In accordance with one aspect of this invention, there is thus provided a brain ventricle shunt system with a flow-rate switching mechanism. The system comprises a brain ventricle catheter which is adapted to be inserted at a tip portion thereof into the brain ventricle so as to drain cerebro-spinal fluid from the brain ventricle, a peritoneum or auricle catheter which is adapted to be inserted at a tip portion thereof into the peritoneum or the auricle so as to feed the cerebro-spinal fluid into the peritoneum or the auricle, and a shunt main body connected at one end to a base portion of the brain ventricle catheter and at the other end to a base portion of the peritoneum or auricle catheter so as to communicate the brain ventricle catheter and the peritoneum or auricle catheter with each other. The system is also provided with a check valve for preventing the cerebro-spinal fluid from flowing back from the peritoneum or auricle catheter to the brain ventricle catheter. The flow-rate switching mechanism is provided with the shunt main body so as to properly control or alter the flow rate of the cerebro-spinal fluid which flows from the brain ventricle to the peritoneum or the auricle. The flow-rate switching mechanism is provided with a plurality of flow passages connected to one another in parallel, a similar plural number of flow-rate regulators interposed respectively in the flow passages so as to control the flow rates through the respective flow passages to predetermined flow rates, and a similar plural number of ON-OFF valves interposed respectively in the plurality of flow passages so as to individually shut off the flow passages upon the application of suitable external drive forces thereto.

In the above-described brain ventricle shunt system of this invention, the plurality OF ON-OFF valves interposed in the plurality of flow passages within the shunt main body are independently controlled in an ON-OFF manner by opening or closing the ON-OFF valves by means of suitable external drive forces, whereby the plurality of flow passages are individually controlled so as to be in communication with each other, or fluidically isolated from each other, so as to suitably control the flow rate of the cerebro-spinal fluid. The flow rate of the cerebro-spinal fluid is equal to the sum of the individual flow rates regulated by means of the flow-rate regulators interposed in their communicating flow passages.

The brain ventricle shunt system of this invention has a merit in that the switching operation of the flow rate, which has heretofore been considered difficult, can in fact be achieved very easily and safely. It permits switching of flow rate of the cerebro-spinal fluid between many levels or values without failure, and the flow-rate controlling position can be precisely determined either visually or palpably through the scalp.

BRIEF DESCRIPTION OF THE DRAWINGS

Various other objects, features, and attendant advantages of the present invention can be better appreciated from the following detailed description when considered in connection with the accompanying drawings, in which like reference characters designate like or corresponding parts throughout the several views, and wherein:

FIGS. 1–6 show a brain ventricle shunt system equipped with a flow-rate switching mechanism, according to a first embodiment of this invention, in which:

FIG. 1 is a partly cross-sectional plan view showing the brain ventricle shunt system without an upper wall thereof and seen in a direction indicated by arrows I,I in FIG. 2;

FIG. 2 is a vertical cross-section of the brain ventricle shunt system, seen in a direction indicated by arrows II,II in FIG. 1;

FIG. 3(a) is a cross-sectional view seen in a direction indicated by arrows III,III in FIG. 1;

FIGS. 3(b)-3(d) are schematic illustrations showing the operation of the brain ventricle shunt system during its implanted state;

FIG. 4 is a cross-sectional view seen in a direction indicated by arrows IV,IV in FIGS. 1 and 7;

FIG. 5 is a cross-sectional view seen in a direction indicated by arrows V,V in FIGS. 1 and 7;

FIG. 6 is a partly cross-sectional plan view showing, on an enlarged scale, a member equipped with a relief valve (hereinafter called "relief-valved member");

FIGS. 7-11 illustrate a brain ventricle shunt system equipped with a flow-rate switching mechanism, according to a second embodiment of this invention, in which:

FIG. 7 is a partly cross-sectional plan view showing the brain ventricle shunt system of the second embodiment without an upper wall thereof and seen in a direction indicated by arrows VII,VII in FIG. 8;

FIG. 8 is a vertical cross-section of the brain ventricle shunt system, seen in a direction indicated by arrows VIII,VIII in FIG. 7;

FIG. 9 is a cross-sectional view seen in a direction indicated by arrows IX,IX in FIG. 7;

FIG. 10 is a cross-sectional view seen in a direction indicated by arrows X,X in FIG. 7;

FIG. 11(a) is a cross-sectional view seen in a direction indicated by arrows XI,XI in FIG. 7; and FIGS. 11(b)-11(d) are schematic illustrations showing the operation of the brain ventricle shunt system of the second embodiment during its implanted state;

FIGS. 12-16 depict a brain ventricle shunt system equipped with a flow-rate switching mechanism, according to a third embodiment of this invention, in which:

FIG. 12 is a plan view of the brain ventricle shunt system of the third embodiment without an upper wall thereof;

FIG. 13 is a cross-sectional view seen in a direction indicated by arrows XIII,XIII in FIG. 12;

FIG. 14 is a cross-sectional view seen in a direction indicated by arrows XIV,XIV in FIG. 12;

FIG. 15 is a cross-sectional view seen in a direction indicated by arrows XV,XV in FIG. 12; and FIG. 16 is a cross-sectional view showing the manner of movement of a movable ball-type valve plug in correlation with FIG. 14.

DETAILED DESCRIPTION OF THE PREFERRED EMBODIMENTS

Figure 1:
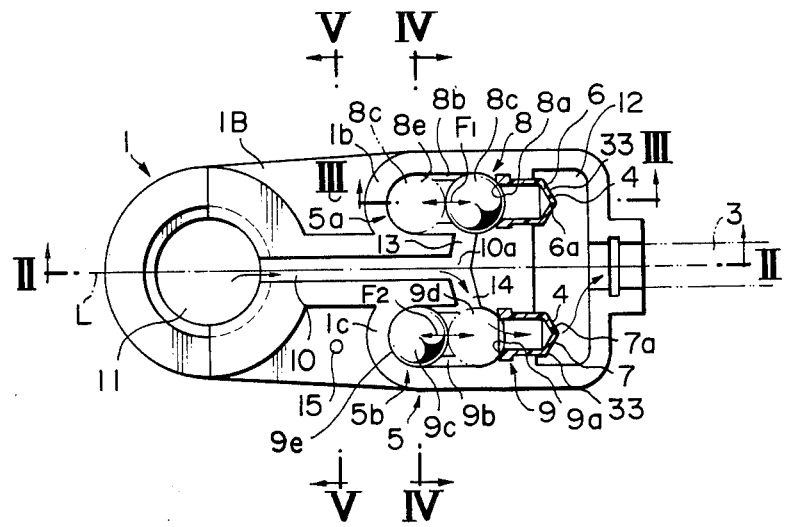
Figure 2:
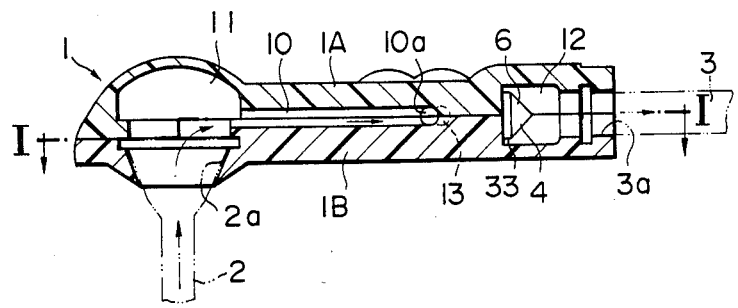
Figure 4:
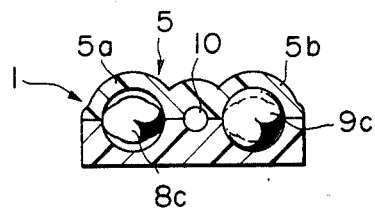
Figure 5:
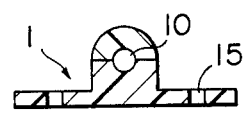

The brain ventricle shunt system according to the first embodiment of this invention comprises, as shown in FIGS. 1-6, a fine tubular brain ventricle catheter 2 which is adapted to be inserted at a tip portion thereof into the brain ventricle of a patient so as to drain cerebro-spinal fluid from the brain ventricle, a peritoneum or auricle catheter (hereinafter called "peritoneum catheter") 3 which is adapted to be inserted at a tip portion thereof into the peritoneum or the auricle of the patient so as to feed the cerebro-spinal fluid into the peritoneum or the auricle, and a shunt main body (relay chamber) 1 which is provided with a main flow passage 10 fluidically interconnecting to a base portion 2a of the brain ventricle catheter 2 and a base portion 3a of the peritoneum catheter 3 so as to provide fluidic communication between both catheters 2,3, shunt main body 1 being formed so as to have soft walls from a suitable silicon resin or the like.

The shunt main body 1 is provided with a pair of check valves 4 which can prevent cerebro-spinal fluid from flowing back from the peritoneum catheter 3 to the brain ventricle catheter 2. In this embodiment, slit-type relief valves 6,7 serving as flow-rate regulators for a flow-rate switching mechanism 5, which will be described below, are an exemplary type of check valve 4.

Figure 6:
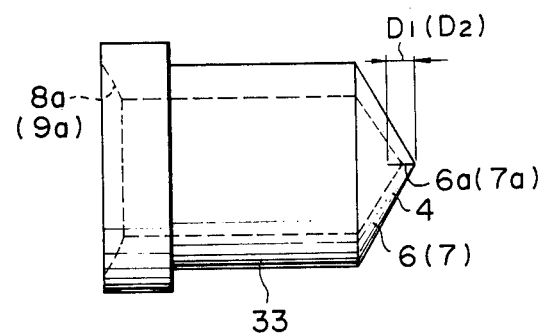
Figure 7:
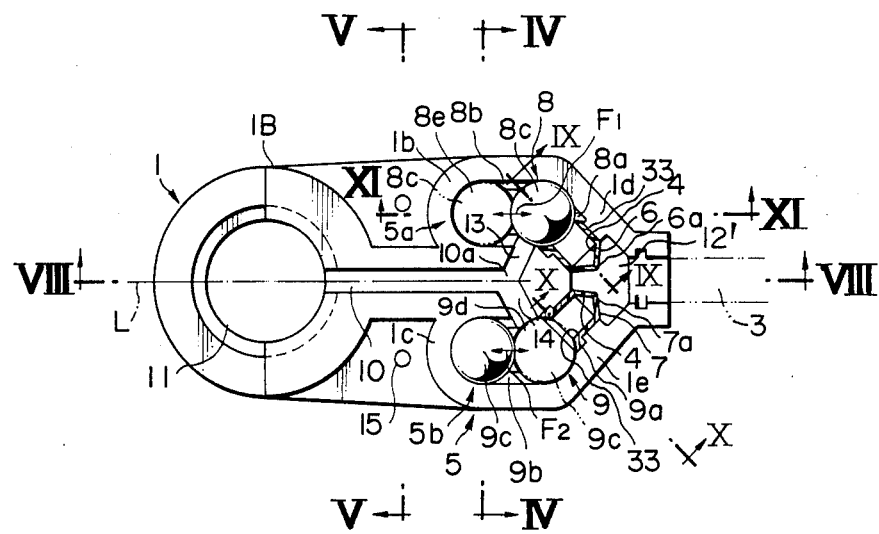
Figure 8:
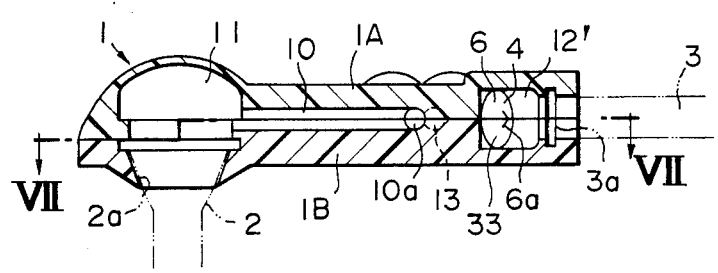
Figure 9:
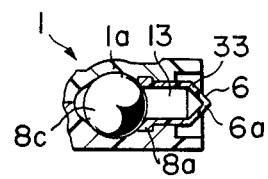
Figure 10:

These slit-type relief valves 6,7 are formed integrally with valves 8a,9a respectively as illustrated in FIG. 6, thereby forming a relief-valve member 33. The relief-valve member 33 is bonded in such a way that it is held between upper and lower parts 1A,1B of the shunt main body 1.

The shunt main body 1 is fixed on the skull 17 under the scalp 16 by stitching the scalp 16 with a suture or the like, which extends through a suture through-hole 15. The shunt main body 1 thus comprises the main flow passage 10 connected respectively to the above-described brain ventricle catheter 2 and the peritoneum catheter 3, a reservoir 11 formed as a small compartment in the shunt main body 1 on the side of the brain ventricle catheter 2 so as to fluidically interconnect passage 10 and catheter 2, a small compartment 12 formed in the shunt main body 1 on the side of the peritoneum catheter 3 so as to fluidically interconnect passage 10 and catheter 3, and first and second branch flow passages 13,14 extending in opposite direction with respect to each other and upon opposite sides of the main flow passage 10 so as to fluidically interconnect the peritoneum catheter end 10a of main flow passage 10 and the small compartment 12 with each other.

As depicted in FIGS. 1 and 6, the first branch flow passage 13 is provided with slit-type relief valve 6 so as to define a first flow-rate regulator relief valve 6 defining a slit 6a of a predetermined depth $D_1$ for controlling the flow rate to a predetermined flow rate $Q_1$ when the first flow passage 13 is in a communicating state, and a ball-type ON-OFF valve 8 which is adapted to shut off the first flow passage 13 upon reception of a driving force from the outside of the shunt main body 1.

The ball-type ON-OFF valve 8 is constructed of a first hemispherical valve seat 8a formed in a wall of the shunt main body 1, a valve chest 8b extending longitudinally in the first flow passage 13, a movable ball-type valve plug 8c enclosed within the valve chest 8b and being movable upon reception of an external driving force, such as, for example a finger 18 which force may be applied through the soft upper and front walls 1a,1b of the valve chest 8b and the scalp 16, a second hemispherical valve seat 8d for holding the valve plug 8c at the closed position (hereinafter called "closed-position holding hemispherical seat 8d") for allowing the valve plug 8c to seat thereon whereby the valve plug 8c is held between the hemispherical seat 8d and the soft upper wall 1a at a position registered with the valve seat 8a so as to close the ON-OFF valve 8 and to shut off the first flow passage 13, and a third hemispherical valve seat 8e for holding the valve plug 8c at the opened position (hereinafter called "opened-position holding hemispherical seat 8e") for allowing the valve plug 8c to seat thereon whereby the valve plug 8c is held between the hemispherical seat 8e and the soft upper wall 1a at a position remote from the valve seat 8a so as to open the ON-OFF valve 8 and to permit communication of the first flow passage 13 with the small compartment 12.

As is also shown in FIG. 6, the second flow passage 14 is provided with slit-type relief valve 7 so as to define a second flow-rate regulator, said relief valve 7 defining a slit 7a of a predetermined depth $D_2(<D_1)$ for controlling the flow rate to a predetermined flow rate $Q_2$ (in the illustrated embodiment, $Q_2 = \frac{1}{2}Q_1$) when the second flow passage 14 is in a communicating state, and a ball-type ON-OFF valve 9 which is adapted to shut off the second flow passage 14 upon reception of a driving force from the outside of the shunt main body 1.

The ball-type ON-OFF valve 9 is constructed of a hemispherical valve seat 9a formed in a wall of the shunt main body 1, a valve chest 9b extending longitudinally in the second flow passage 14, a movable ball-type valve plug 9c enclosed within the valve chest 9b and being movable upon reception of an external driving force, such as, for example the finger 18 which force may be applied through the soft upper and front walls 1a and 1c of the valve chest 9b and the scalp 16, a closed-position holding hemispherical valve seat 9d for allowing the valve plug 9c to seat thereon whereby the valve plug 9c is held between the hemispherical seat 9d and the soft upper wall 1a at a position registered with the valve seat 9a so as to close the ON-OFF valve 9 and to shut off the second flow passage 14, and an opened-position holding hemispherical seat 9e for allowing the valve plug 9c to seat thereon whereby the valve plug 9c is held between the hemispherical seat 9e and the soft upper wall 1a at a position remote from the valve seat 9a so as to open the ON-OFF valve 9 and to permit communication of the second flow passage 14 with the small compartment 12. Namely, the ball-type ON-OFF valve 9 is constructed substantially in the same manner as the above-described ball-type ON-OFF valve 8.

The first relief valve 6 has a regulated flow rate greater than that of the second relief valve 7. In the present embodiment, the relief valves 6,7 are both constructed as single slit-type check valves. They may however be replaced by cruciform-slit-type, spring-type or membrane-type check valves.

As the material for the movable ball-type valve plugs 8c,9c, a plastic or metallic material may be used. It is also possible to use a metal ball with a silicone coating applied thereon. In the case of plastic movable ball-type valve plugs, it is desirable to mix a contrast medium with the plastic material so as to permit determination of the positions of the movable ball-type valve plugs 8c,9c by means of an X-ray picture in the same manner as in the case of metal movable ball-type valve plugs.

Continuing further, the flow-rate switching mechanism 5 is comprised of a first flow-rate switching part 5a provided with the slit-type relief valve 6 and ball-type ON-OFF valve 8 which are both interposed in the flow passage 13 in order to control the flow rate to the predetermined flow rate $Q_1$, as well as a second flow-rate switching part 5b provided with the slit-type relief valve 7 and ball-type ON-OFF valve 9 which are both interposed in the flow passage 14 in order to control the flow rate to the predetermined flow rate $Q_2$ ($=\frac{1}{2}Q_1$). The flow-rate switching mechanism 5 is also constructed in such a way that the moving directions $F_1, F_2$ of the valve plugs 8c,9c in these ON-OFF valves 8,9 are parallel to each other and extend parallel to the central axis L of the shunt main body 1.

Since the brain ventricle system according to the first embodiment of this invention is constructed as described above, when the movable ball-type valve plugs 8c,9c are caused to seat on their corresponding open-position holding hemispherical seats 8e,9e as illustrated in FIG. 3(d), the cerebro-spinal fluid which has flowed into the reservoir 11 from the brain ventricle of a patient by way of the brain ventricle catheter 2 passes through the main flow passage 10 and first and second flow passages 13,14 into the valve chests 8b,9b and then flows further through the two ON-OFF valves 8,9, each of which is in its open state, to positions upstream of the relief valves 6,7.

If there is a difference greater than a predetermined value between the pressure of the cerebro-spinal fluid on the upstream side of the relief valves 6,7 and that of the cerebro-spinal fluid on the downstream side of the relief valves 6,7 at this time, the relief valves 6,7 are maintained in their open state so that the cerebro-spinal fluid is caused to flow out into the small compartment 12. The cerebro-spinal fluid in the small compartment 12 is then caused to flow further into the peritoneum of the patient or into the auricle of the patient by way of the peritoneum catheter 3.

In the manner described above, the cerebro-spinal fluid from the brain ventricle is allowed to flow at a maximum flow rate, which is the sum $(Q_1+Q_2)$ of the regulated flow rates of the two relief valves 6,7.

When it is desired to change the flow rate to an intermediate flow rate, that is, $Q_1$, it is only necessary to have the movable ball-type valve plug 8c seated on the hemispherical seat 8e so as to maintain the first ON-OFF valve 8 open and at the same time to have the movable ball-type valve plug 9c seated on the hemispherical seat 9d so as to close the second ON-OFF valve 9 as shown by phantom lines in FIG. 1. In this manner, the cerebro-spinal fluid is allowed to flow only through the first relief valve 6 having the relatively large regulated flow rate.

When it is desired to change the flow rate to a still smaller flow rate, that is, $Q_2$, it is only necessary to have the movable ball-type valve plug 8c seated on the hemispherical seat 8d so as to close the first ON-OFF valve 8 and at the same time to have the movable ball-type valve plug 9c seated on the hemispherical seat 9e so as to maintain the second ON-OFF valve 9 open as indicated by the solid lines in FIG. 1. In this manner, the cerebro-spinal fluid is allowed to flow only through the second relief valve 7 having the relatively small regulated flow rate.

Since the first and second relief valves 6,7 have different regulated flow rates in this embodiment as described above, the flow rate can be switched between three different levels by means of the two relief valves 6,7. Even when both relief valves 6,7 have the same regulated flow rate, the flow rate can be switched over between two different levels, namely, by causing the cerebro-spinal fluid to flow through either one of the valves 6,7 or through both of the valves 6,7.

When it is desired to stop the drainage of the cerebro-spinal fluid through the brain ventrical shunt, it is only necessary to guide the movable ball-type valve plugs 8c,9c to their corresponding closed-position holding hemispherical seats 8d,9d so as to close both the first and second ON-OFF valves 8,9 and thereby shut off the flow of the cerebro-spinal fluid from the reservoir 11 through the main flow passage 10 and first and second branch flow passages 13,14 to the relief valves 6,7.

As depicted in FIGS. 3(a)–3(d), it is only necessary to press the soft upper wall 1a by means of the finger 18 through the scalp 16 when it is desired to move the valve plugs 8c,9c from the closed-position holding hemispherical seats 8d,9d toward the opened-position holding hemispherical seats 8e,9e in the first embodiment.

When it is desired to move the valve plugs 8c,9c from the opened-position holding hemispherical seats 8e,9e toward the closed-position holding hemispherical seats 8d,9d, it is only necessary to press the soft upper wall 1a and soft front walls 1b,1c by means of the finger 18 through the scalp 16.

Since the moving directions $F_1,F_2$ of the valve plugs 8c,9c are designed to be parallel to each other in the first embodiment, it is easy to determine visually or palpably whether the ON-OFF valves 8,9 are open or closed.

The brain ventricle shunt system provided with a flow-rate switching mechanism, which relates to the second embodiment of this invention, is constructed as shown in FIGS. 7-11. It is different from the first embodiment in the following points.

The valve seats 8a,9a facing the valve chests 8b,9b of the ball-type ON-OFF valves 8,9 are designed to extend in directions inclined with respect to the moving directions $F_1,F_2$ of their corresponding valve plug 8c,9c.

Namely, the first and second flow passages 13,14 are formed respectively along lines which connect the center of a small compartment 12′ and the central positions of the hemispherical seats 8d,9d, and along these lines or directions extend soft rear walls 1d,1e which constitute the outer wall of the shunt main body 1.

The remaining structure is the same as in the first embodiment. In FIGS. 7-11, like reference numerals identify substantially similar elements of structure as in FIGS. 1-6.

As shown in FIGS. 11(a)-11(d), it is only necessary to press the soft upper wall 1a and soft rear walls 1d,1e by means of a finger 18 acting upon the scalp 16 when it is desired to move the valve plugs 8c,9c from the closed-position holding hemispherical seats 8d,9d toward the opened-position holding hemispherical seats 8e,9e in the second embodiment. It is hence possible to apply greater lateral drive forces to the valve plugs 8c,9c as is compared with the first embodiment.

It is also possible to provide three or more flow-rate switching parts of the above-described type with the regulated flow rates of said switching parts being set at levels different from one another. If the flow-rate switching parts are provided successively with regulated flow rates set, for example, at $Q \times 2^n$ in which Q means the minimum flow rate and n denotes natural numbers, the flow rate can be switched over among the $(2^n-1)$ levels.

In the above-described first and second embodiments, the first and second flow-rate switching parts 5a,5b may be constructed in such a way that the moving directions $F_1,F_2$ of the valve plugs 8c,9c extend at right and angles with respect to the central axis L of the shunt main body 1. Further, the valve chests 8b,9b and small compartments 12,12′ may be arranged in a vertical relationship.

In the brain ventricle shunt system according to the third embodiment of this invention, the shunt main body (relay chamber) 1 formed so as to have soft walls made of a insuitable silicon resin or the like is provided with the reservoir 11 in the form of a small compartment and a valve chest 20 fluidically communicating with the reservoir 11 as shown in FIGS. 12-16. The fine tubular brain ventricle catheter 2, which is adapted to be inserted into the brain ventricle of a patient, is connected to the reservoir 11.

At the other end, the shunt main body 1 is connected to the peritoneum catheter 3. A partition wall 21 is provided within shunt main body 1 so as to divided the interior of the shunt main body 1 into an upstream-side compartment 27 and a downstream-side compartment 28 as seen in FIGS. 13-15. The upstream-side compartment 27 is in fluidic communication with the brain ventricle catheter 2, while the downstream-side compartment 28 is in fluidic communication with the peritoneum catheter 3.

In horizontally expanded parts of the valve chest 20, the partition wall 21 is provided with a first check valve (relief valve) 4a which serves as the first flow-rate regulator (see FIGS. 12 and 15) and a second check valve (relief valve) 4b which serves as the second flow-rate regulator. The first and second check valves 4a,4b are closed and opened by the pressure of cerebro-spinal fluid, a liquid excrement from the brain ventricle of a patient, when the cerebro-spinal fluid has flowed through the brain ventricle catheter 2 and reservoir 11 into the upstream-side compartment 27 of the valve chest 20.

In the upstream-side compartment 27, the partition wall 21 is provided with hemispherical valve seats 22,23 which surround the check valves 4a,4b respectively. A single movable ball-type valve plug 24, which is brought into engagement with either one of the valve seats 22,23 to selectively open or close the corresponding check valve 4a or 4b and constitutes a part of the flow-rate switching mechanism, is enclosed within the upstream-side compartment 27 in such a way that the valve plug 24 is movable upon receipt of a driving force by means of, for example a finger or the like from the outside of the soft wall of the valve chest 20. An ON-OFF valve is thus formed by the valve plug 24 and both valve seats 22,23.

Furthermore, an additional hemispherical seat 25 which is adapted to have the movable ball-type valve plug 24 seated thereon is formed in the surface of the partition wall 21 in the upstream-side compartment 27 at a position centrally between the first check valve 4a and second check valve 4b.

When the movable ball-type valve plug 24 has been seated on either one of the valve seats 22,23 or the hemispherical seat 25, it is held between the seat and the soft wall of the valve chest 20 so that the movable ball-type valve plug 24 is held in place.

Between the reservoir 11 and hemispherical seat 25, a valve plug holding part 26 is provided as a valve seat defined in the soft wall of the upstream-side compartment 27 and the partition wall 21. By pressing the movable ball-type valve plug 24 into the holding part 26, the stream of the liquid flowing from the reservoir 11 to the check valves 4a,4b in the upstream-side compartment 27 of the valve chest 20 is terminated. A cutoff valve is thus formed by the valve plug 24 and holding part 26.

The movable ball-type valve plug 24 is made of a material substantially the same as the valve plugs 8c,9c in the above-described first and second embodiments.

Since the brain ventricle shunt according to the third embodiment of the present invention is constructed as described above, the cerebro-spinal fluid which has flowed from the brain ventricle of a patient into the reservoir 11 through the brain ventricle catheter 2 enters the upstream-side compartment 27 of the valve chest 20 and then passes through the two check valves 4a,4b into the downstream-side compartment 28 as shown in FIGS. 13–15 when the movable ball-type valve plug 24 is caused to be seated on the hemispherical seat 25.

Then, the cerebro-spinal fluid in the downstream-side compartment 28 flows into the peritoneum of the patient by way of the peritoneum catheter 3.

In the above-described manner, the liquid excrement from the brain ventricle is allowed to flow at the maximum flow rate as the sum of the regulated flow rates of the two check valves 4a,4b.

When it is desired to change the flow rate to an intermediate flow rate, it is only necessary to cause the movable ball-type valve plug 24 to seat on the valve seat 23 disposed in the flow passage of the second check valve 4b so as to close the check valve 4b. In this manner, the cerebro-spinal fluid is allowed to flow only through the first check valve 4a having the relatively large regulated flow rate.

When it is desired to reduce the flow rate further, it is only necessary to cause the movable ball-type valve plug 24 to seat on the valve seat 22 associated with the first check valve 4a so as to close the check valve 4a. In this manner, the liquid excrement is allowed to flow only through the second check valve 4b having the relatively small regulated flow rate.

Since the first check valve 4a and second check valve 4b have mutually-different regulated flow rates in the present embodiment as described above, the flow rate can be switched between three different levels by means of the two check valves 4a,4b. Even when both check valves 4a,4b have the same regulated flow rate, the flow rate can be switched between two different levels by causing the liquid excrement to flow through either one of the check valves or through both check valves.

When it is desired to stop the drainage of the liquid excrement through the brain ventricle shunt, it is only necessary to guide the movable ball-type valve plug 24 to the plug holding part 26 so that the flow passage from the reservoir 11 to the valve 20 is closed.

It is also feasible to alter the flow rate between four different levels if three check valves having three different regulated flow rates are provided.

In the present embodiment, the hemispherical valve seats 22,23 for selectively closing the corresponding check valves 4a,4b are respectively provided surrounding the check valves 4a,4b. Instead of these hemispherical valve seats 22,23, hemispherical valve seats capable of forming parts similar to the holding part 26 may be provided at locations along the moving paths of the movable ball-type valve plug 24 between the hemispherical seat 25 and the respective check valves 4a,4b.

In each of the above-described embodiments, orifices having different flow rates may be arranged instead of the check valves 4a,4b and relief valves 6,7. Here, check valves may be interposed in the first and second flow passages 13,14 or a single check valve may be interposed in the main flow passage 10.

Having now fully described the invention, it will be apparent to one of ordinary skill in the art that many changes and modifications can be made thereto without departing from the spirit or scope of the invention as set forth herein.

What is claimed is:

1. In a brain ventricle shunt system with a flowrate switching means, said system comprising a brain ventricle catheter adapted to be inserted at a tip portion thereof into the brain ventricle so as to drain cerebro-spinal fluid from the brain ventricle, a peritoneum or auricle catheter adapted to be inserted at a tip portion thereof into the peritoneum or the auricle so as to feed said cerebro-spinal fluid into said peritoneum or auricle, and a shunt main body connected at one end thereof to a base portion of said brain ventricle catheter and at another end thereof to a base portion of said peritoneum or auricle catheter so as to fluidically communicate said brain ventricle catheter and said peritoneum or auricle catheter with each other, the improvement comprising:
   check valve means disposed within said shunt main body for preventing said cerebro-spinal fluid from flowing back from said peritoneum or auricle catheter to said brain ventricle catheter; and
   flow rate switching means provided within said shunt main body for altering the flow rate of said cerebro-spinal fluid from said brain ventricle catheter to said peritoneum or auricle catheter;
   said flow-rate switching means comprising a predetermined plurality of flow passages connecting said brain ventricle catheter and said peritoneum or auricle catheter, a predetermined plurality of flow rate regulators interposed respectively within said flow passages for controlling the flow rates through said respective flow passages to predetermined flow rates, and a predetermined plurality of ON-OFF valves interposed respectively within said plurality of flow passages so as to individually close said flow passages upon the application of external drive forces thereto.

2. The system as claimed in claim 1, wherein the plurality of flow passages are respectively provided with check valves.

3. The system as claimed in claim 1, wherein at least one of the plural ON-OFF valves is constructed as a ball-type ON-OFF valve provided with a valve seat formed in a wall of the shunt main body, a valve chest formed in the shunt main body positioned upstream of the valve seat, and a movable ball-shaped valve plug enclosed within the valve chest in such a way that the valve plug is movable to a position, where the valve plug is in registration with the valve seat and can close the ON-OFF valve, upon the application of a drive force from the outside of the shunt main body.

4. The system as claimed in claim 3, wherein the valve plugs of the plural ON-OFF valves are provided respectively with the ON-OFF valves in such a way that the valve plugs can be brought into registration with the valve seats of their associated ON-OFF valves.

5. The system as claimed in claim 4, wherein the valve plugs of the plural ON-OFF valves are enclosed within a single valve chest and are formed as a single movable ball-type valve plug which can be brought into registration with the valve seat of each of the ON-OFF valves so as to close any one of the ON-OFF valves selectively.

6. The system as claimed in claim 5, wherein the shunt main body is provided with a partition wall, whereby the interior of the shunt main body is divided into an upstream-side compartment which defines the valve chest communicating with the brain ventricle catheter and a downstream-side compartment communicating with the peritoneum or auricle catheter, and the partition wall is provided with the check valves.

7. The system as claimed in claim 6, wherein a hemispherical seat is provided in the upstream-side compartment of the shunt main body so as to allow the movable ball-type valve plug to seat at a position other than the position where the ON-OFF valve is closed by the valve plug.

8. The system as claimed in claim 6, wherein a holding part capable of holding the movable ball-type valve plug and shutting off any flow to the ON-OFF valve is provided on the upstream side of the ON-OFF valve in the upstream-side compartment of the shunt main body.

9. The system as claimed in claim 3, wherein the plurality of flow-rate regulators control their corresponding flow rates at different levels.

10. The system as claimed in claim 9, wherein the flow rates controlled by the plurality of flow rate-regulatorare set successively at $Q \times 2^n$ in which Q means the minimum flow rate and n denotes natural numbers.

11. The system as claimed in claim 10, wherein at least one of the plurality of flow-rate regulators is formed as a slit-type relief valve which is opened when the pressure of the cerebro-spinal fluid on the upstream side in the flow-rate regulator becomes higher by at least a predetermined pressure than the pressure of the cerebro-spinal fluid on the downstream side in the flow-rate regulator.

12. The system as claimed in claim 10, wherein all of the plurality of flow-rate regulators are formed as slit-type relief valves, each of which is opened when the pressure of the cerebro-spinal fluid on the upstream side in the flow-rate regulator becomes higher by at least a predetermined pressure than the pressure of the cerebro-spinal fluid on the downstream side in the flow-rate regulator, and also serve as the check valves.

13. A brain ventricle shunt system, comprising:
brain ventricle catheter means for insertion into the brain ventricle so as to drain cerebro-spinal fluid from said brain ventricle;
peritoneum or auricle catheter means for insertion into the peritoneum or auricle for feeding said cerebro-spinal fluid into said peritoneum or auricle;
shunt main body means connected at one end thereof to said brain ventricle catheter means and at another end thereof to said peritoneum or auricle catheter means for providing fluidic communication between said brain ventricle catheter means and said peritoneum or auricle catheter means;
first flow passage means, having a first predetermined flow rate, defined within said shunt main body for fluidically connecting said brain ventricle catheter means and said peritoneum or auricle catheter means;
second flow passage means, having a second predetermined flow rate, defined within said shunt main body means for fluidically connecting said brain ventricle catheter means and said peritoneum or auricle catheter means;
said first valve means disposed within said first flow passage means for opening or closing said first flow passage means so as to permit or prevent said cerebro-spinal fluid to flow, or from flowing, from said brain ventricle catheter means to said peritoneum or auricle catheter means at said first predetermined flow rate; and second valve means disposed within said second flow passage means for opening or closing said second flow passage means so as to permit or prevent said cerebro-spinal fluid to flow, or from flowing, from said brain ventricle catheter means to said peritoneum or auricle catheter means at said second predetermined flow rate,
whereby when said first and seciond valve means are both open, said cerebro-spinal fluid flows from said brain ventricle catheter means to said peritoneum or auricle catheter means at a flow rate equal to said first and second predetermined flow rates, while when said first valve means is open and said second valve means is closed, said cerebro-spinal fluid flows from said brain ventricle catheter means to said peritoneum or auricle catheter means at a flow rate equal to said first predetermined flow rate, while when said first valve means is closed and said second valve means is open, said cerebro-spinal flows from said brain ventricle catheter means to said peritoneum or auricle catheter means at a flow rate equal to said second predetermined flow rate, while when said first and second valve means are both closed, no cerebro-spinal fluid flows from said brain ventricle catheter means to said peritoneum or auricle catheter means.

14. A system as set forth in claim 13, wherein:
said first and second flow passage means comprise substantially parallel flow passages defined within said shunt main body.

15. A system as set forth in claim 13, wherein:
said first and second valve means comprise ball check valves.

16. A system as set forth in claim 13, wherein:
said first and second predetermined flow rates are different from each other.

17. A system as set forth in claim 13, wherein:
each of said first and second valve means comprises a first valve seat for maintaining its respective valve at a closed position with respect to its respective flow passage, and a second valve seat for maintaining its respective valve at an open position with respect to its respective flow passage.

18. Fluid flow control apparatus for use in a brain ventricle shunt system, comprising:
first fluid control means for receiving a supply of cerebro-spinal fluid from a brain ventricle;
second fluid conduit means for receiving said cerebro-spinal fluid from said first fluid conduit means and for feeding said cerebro-spinal fluid to a peritoneum or auricle;
housing means connected at one end thereof to said first fluid conduit means and at another end thereof to said seciond fluid conduit means for providing fluidic communication between said first and second fluid conduit means;
first fluid flow passage means, having a first predetermined flow rate, defined within said housing means for fluidically connecting said first and second fluid conduit means;
second fluid flow passage means, having a second predetermined flow rate, defined within said housing means for fluidically connecting said first and second fluid conduit means;
first valve means disposed within said first fluid flow passage means for opening or closing said first fluid flow passage means so as to permit or prevent said fluid to flow, or from flowing, from said first fluid conduit means to said second fluid conduit means at said first predetermined flow rate; and
second valve means disposed within said second fluid flow passage means for opening or closing said second fluid flow passage means so as to permit or prevent said fluid to flow, or from flowing, from said first fluid conduit means to said second fluid conduit means at said second predetermined flow rate, whereby when said first and second valve means are both open, said fluid flows from said first fluid conduit means to said second fluid conduit means at a flow rate equal to said first and second predetermined flow rate, while when said first valve means is open and said second valve means is closed, said fluid flows from said first fluid conduit means to said second fluid conduit means at a flow rate equal to said first predetermined flow rate, while when said first valve means is closed and said second valve means is open, said fluid flows from said first fluid conduit means to said second fluid conduit means at a flow rate equal to said second predetermined flow rate, while when said first and second valve means are both closed, no fluid flows from said first fluid conduit means to said second fluid conduit means.

19. Control apparatus as set forth in claim 18, wherein:
said first and second predetermined flow rates are different from each other whereby three different fluid flow rates of said fluid from said first fluid conduit means to said second fluid conduit means are achieved depending upon the open or closed positions of said first and second valve means.

20. Control apparatus as set forth in claim 18, wherein:
each of said first and second valve means comprises a ball check valve, a first valve seat for maintaining each of said ball check valves at a closed position with respect to said first and second fluid flow passage means, and a second valve seat for maintaining each of said ball check valves at an open position with respect to said first and second fluid flow passage means.

* * * * *